US008440413B2

(12) United States Patent
Yodoi et al.

(10) Patent No.: US 8,440,413 B2
(45) Date of Patent: May 14, 2013

(54) METHOD OF SCREENING FOR A SUBSTANCE THAT STRENGTHENS A BOND BETWEEN THIOREDOXIN AND MACROPHAGE MIGRATION INHIBITION FACTOR

(75) Inventors: Junji Yodoi, Kyoto (JP); Norihiko Kondo, Yokohama (JP); Aoi Son, Kyoto (JP); Noriko Kato, Ashiya (JP); Tomijiro Hara, Higashimurayama (JP); Tomohisa Horibe, Kyoto (JP)

(73) Assignee: Redox Bioscience, Inc., Kyoto (JP)

( * ) Notice: Subject to any disclaimer, the term of this patent is extended or adjusted under 35 U.S.C. 154(b) by 0 days.

(21) Appl. No.: 13/131,339

(22) PCT Filed: Nov. 26, 2009

(86) PCT No.: PCT/JP2009/069985
§ 371 (c)(1),
(2), (4) Date: Aug. 15, 2011

(87) PCT Pub. No.: WO2010/061902
PCT Pub. Date: Jun. 3, 2010

(65) Prior Publication Data
US 2012/0003673 A1 Jan. 5, 2012

Related U.S. Application Data

(63) Continuation-in-part of application No. 12/315,069, filed on Nov. 26, 2008, now abandoned, which is a continuation-in-part of application No. PCT/JP2007/060557, filed on May 23, 2007.

(30) Foreign Application Priority Data

May 29, 2006 (JP) ................................ 2006-148844

(51) Int. Cl.
*G01N 33/53* (2006.01)
*C07K 14/52* (2006.01)
(52) U.S. Cl.
USPC ........................................... 435/7.1; 530/351

(58) Field of Classification Search ....................... None
See application file for complete search history.

(56) References Cited

U.S. PATENT DOCUMENTS

2012/0003673 A1* 1/2012 Yodoi et al. ................. 435/7.92

FOREIGN PATENT DOCUMENTS

| | | | |
|---|---|---|---|
| JP | 62019532 | A | 1/1987 |
| JP | 1085097 | A | 3/1989 |
| JP | 3204818 | A | 9/1991 |
| JP | 5139992 | A | 6/1993 |
| JP | 2000103743 | A | 4/2000 |
| JP | 2001322929 | A | 11/2001 |
| JP | 2002179588 | A | 6/2002 |
| JP | 2004067542 | A | 3/2004 |
| JP | 2005060408 | A | 3/2005 |
| JP | 2005225853 | A | 8/2005 |
| JP | 2006109754 | A | 4/2006 |
| JP | 2006151861 | A | 6/2006 |
| JP | WO2007138961 | A1 | 12/2007 |

OTHER PUBLICATIONS

Son et al (2009. Antioxidants & Redox Signaling. 11(10): 2595-2605).*
Cvetkovic et al, 2006. International Immunopharmacology. 6: 1527-1534.*
Bernhagen et al. "MIF is a pituitary-derived cytokine that potentiates lethal endotoxaemia" Nature, 1993, vol. 365, pp. 756-759.
Bork et al. "Powers and pitfalls in sequence analysis: the 70% hurdle" Eur Molecul Biol, 2000, vol. 10, pp. 398-400.
Brenner et al. "Errors in genome annotation" Trend in Genet, 1999, vol. 15, pp. 132-133.
Bucala et al. "MIF rediscovered:cytokine, pituitary hormone, and glucocorticoid-induced regulator of the immune response" FASEB J, 1996, vol. 10, pp. 1607-1613.
Calandra et al. "MIF as a glucocorticoid-induced modulator of cytokine production" Nature, 1995, vol. 377, pp. 68-71.
Doerks et al. "Protein annotation:detective work for function prediction" Trend Genet, 1998, vol. 14, pp. 248-250.
Donnelly et al. "Regulatory role for macrophage migration inhibitory factor in acute respiratory distress syndrome" Nat Med, 1997, vol. 3, pp. 320-323.
Gaster et al. "Chapter 3:Latest Developments in Serotonin Receptor Modulation" Ann Repor Med Chem, 1998, 33rd book, pp. 21-30.
Hirota et al."AP-1 transcriptional activity is regulated by a direct association between thioredoxin and Ref-1" Proc Natl Acad Sci USA, 1997, vol. 94, pp. 3633-3638.
Ichiyama et al. "Inhibition of joint inflammation and destruction induced by anti-type II collagen antibody/lipopolysaccharide(LPS)-induced arthritis in mice due to deletion of macrophage migration inhibitory factor (MIF)" Cytokine, 2004, vol. 26, pp. 187-194.
Kato et al. "Cell surface thioredoxin(TRX) is involved in macrophage migration inhibitory factor (MIF)-mediated inflammatory responses" Japan Soc Immunol/Report, 2007,vol. 37, p. 230 (3-C-W36-24-P), lines 1-2 and 5-7.

(Continued)

*Primary Examiner* — Zachary Howard
(74) *Attorney, Agent, or Firm* — Lawson & Weitzen, LLP; Sonia K. Guterman; Teofilo Javier, Jr.

(57) ABSTRACT

Disclosed is a screening method which can select a substance having an influence on the binding between thioredoxin and MIF. The screening method is characterized in that a test substance capable of enhancing the binding between a polypeptide belonging to the thioredoxin family and a macrophage migration inhibitory factor is selected through the steps of mixing at least one binding substance selected from the substances (1) to (4) shown below with the test substance, allowing the binding substance to bind to the macrophage migration inhibitory factor, and confirming the binding between the binding substance and the macrophage migration inhibitory factor: (1) a polypeptide belonging to the thioredoxin family; (2) a protein which comprises an amino acid sequence produced by deleting, substituting or adding one or several amino acid residues in an amino acid sequence for a polypeptide belonging to the thioredoxin family and has the same activity as that of a polypeptide belonging to the thioredoxin family; (3) a gene encoding the polypeptide (1); and (4) a gene encoding the protein (2).

2 Claims, 11 Drawing Sheets

OTHER PUBLICATIONS

Kobayashi et al. "Prevention of lethal acute hepatic failure by antimacrophage migration inhibitory factor antibody in mice treated with Bacille Calmette-Guerin and Lipopolysaccharide" Hepatology, 1999, vol. 29, pp. 1752-1759.

Kondo et al. "Redox-Sensing Release of Human Thioredoxin from T Lymphocytes with Negative Feedback Loops" J Immunol, 2004, vol. 172, pp. 442-448.

Lan et al. "The Pathogenic Role of Macrophage Migration Inhibitory Factor in Immunologically Induced Kidney Disease in the Rat" J Exp Med, 1997, vol. 185, pp. 1455-1465.

Leung et al. "Anti-macrophage migration inhibitory factor reduces transforming growth factor-beta1 expression in experimental IgA nephropathy" Nephroi Dial Transplant, 2004, vol. 19, pp. 1976-1985.

Liu et al. "Thioredoxin promotes ASK1 ubiquitination and degradation to inhibit ASK1-mediated apoptosis in a redox activity-independent manner" Circul Res, 2002, vol. 90, pp. 1259-1266.

Makita et al. "Effect of anti-macrophage migration inhibitory factor antibody on lipopolysaccharide-induced pulmonary neutrophil accumulation" Am J Respir Crit Care Med, 1998. vol. 158, pp. 573-579.

Metz et al. "Role of macrophage migration inhibitory factor in the regulation of the immune response" Adv Immunol, 1997,vol. 66, pp. 197-223.

Mikulowska et al. "Macrophage migration inhibitory factor is involved in the pathogenesis of collagen type II-induced arthritis in mice" J Immunol, 1997, vol. 158, pp. 5514-5517.

Mizue et al. "Role for macrophage migration inhibitory factor in asthma" Proc Natl Acad Sci, 2005, vol. 102, pp. 14410-14415.

Nakamura et al. "Redox regulation of cellular activation" Annu Rev Immunol, 1997, vol. 15, pp. 351-369.

Nakamura et al. "Circulating thioredoxin suppresses lipopolysaccharide-induced neutrophil chemotaxis" Proc Natl Acad Sci, 2001, vol. 98, pp. 15143-15148.

Ngo et al. "Chapter 14: Computational complexity, protein structure prediction, and the levinthal paradox," The Protein Folding Problem and Tertiary Structure Prediction, pp. 433-440 and 492-495,ed by Merz et al, 1994.

Nishihira "Novel pathophysiological aspects of macrophage migration inhibitory factor (review)" Intl J Mol Med, 1998, vol. 2, pp. 17-28.

Nishihira Macrophage migration inhibitory factor (MIF): Its essential role in the immune system and cell growth, J Interferon Cytokine Res, 2000, vol. 20,pp. 751-762.

Skolnick et al. "From genes to protein structure and function: novel applications of computational approaches in the genomic era" Trends in Biotech, 2000, vol. 18, pp. 34-39.

Tagaya et al. "ATL-derived factor (ADF), an IL-2 receptor/Tac inducer homologous to thioredoxin; possible involvement of dithiol-reduction in the IL-2 receptor induction" The EMBO J, 1989, vol. 8, pp. 757-764.

Tsuji et al. "Thioredoxin protects against joint destruction in a murine arthritis model" Free Radic Biol Med, 2006, vol. 40, pp. 1721-1731.

Wells et al. "Additivity of mutational effects in proteins" Biochemistry, 1990, vol. 29, pp. 8509-8517.

Yang et al. "Reversal of established rat crescentic glomerulonephritis by blockade of macrophage migration inhibitory factor(MIF): Potential role of MIF in regulating glucocorticoid production" Mol Med,1998, vol. 4, pp. 413-424.

Arai et al. "Thioredoxin-1 promotes survival in cells exposed to S-nitrosoglutathione: Correlation with reduction of intracellular levels of nitrosothiols and up-regulation of the ERK1/2 MAP Kinases" Toxicol Appl Pharm, 2008, vol. 233, pp. 227-237.

Yamamoto et al. "Induction of Human Thioredoxin in Cultured Human Retinal Pigment Epithelial Cells through Cyclic AMP-dependent Pathway; Involvement in the Cytoprotective Activity of Prostaglandin E" Exp Eye Res, 1997, vol. 65, pp. 645-652.

* cited by examiner

Fig1
Confirmatory experiment of the bond betweeen
TRX and MIF in ATL2/HL60 cells
immunoprocipitation experiment
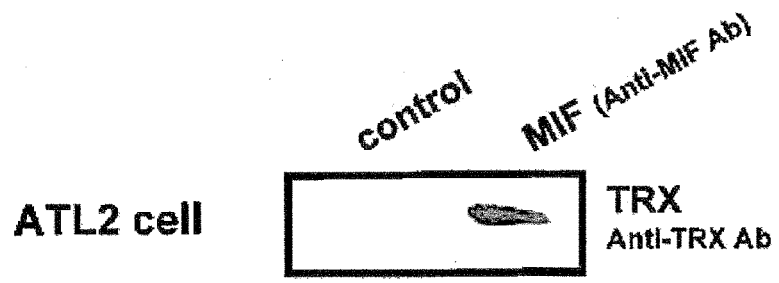
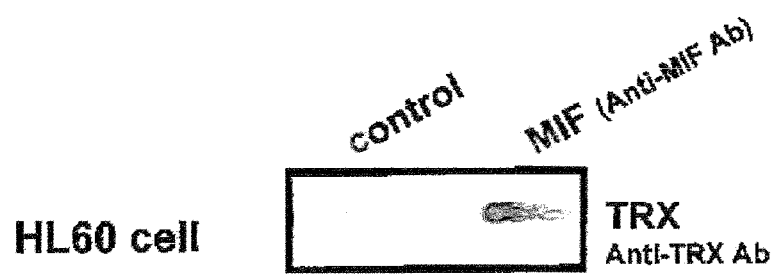

METHOD OF SCREENING FOR A SUBSTANCE THAT STRENGTHENS A BOND BETWEEN THIOREDOXIN AND MACROPHAGE MIGRATION INHIBITION FACTOR

RELATED APPLICATIONS

This application is a national phase application of international application serial number PCT/JP2009/069985 filed Nov. 26, 2009 which claims the benefit of U.S. utility application Ser. No. 12/315,069 filed Nov. 26, 2008, which is a continuation-in-part of international application serial number PCT/JP2007/060557 filed May 23, 2007, which claims the benefit of Japanese application serial number 2006-148844 filed May 29, 2006, all of which are hereby incorporated herein by reference in their entireties.

FIELD OF THE INVENTION

The present invention relates to a screening method for selecting a test substance which strengthens a bond between a polypeptide of a thioredoxin family (hereinafter, referred to as "TRXs") and a macrophage migration inhibition factor (hereinafter, referred to as "MIF"). The present invention further relates to a composition comprising the substance chosen in the method thereof, and a binding substance.

DESCRIPTION OF THE BACKGROUND ART

A macrophage migration inhibitory factor (MIF) is an inflammatory cytokine that inhibits random migration of macrophages to inflammatory regions, and plays an important role in systemic/local inflammation and immune responses (Nishihira J., J Interferon Cytokine Res, (2000) 20:751-762; Bucala R., FASEB J (1996)7:19-24).

MIF has been reported to be produced by immunocompetent cells (for example, lymphocytes and macrophages) and a pituitary in response to biological invasion (for example, stimulations by oxidative stress-inducing endotoxin, active oxygen and ultraviolet light), located upstream of inflammatory cytokine cascade, and control inflammatory reactions (by inducing expressions of other inflammatory cytokines) (Annual Reports in Medical Chemistry, Volume 33, Page 24, 1998; Advances in Immunology, Volume 66, Page 197, 1997).

MIF has also been reported to play important roles in various biological reactions; (1) it inhibits the anti inflammatory effect of glucocorticoids to promote the inflammation: (2) it is a T-lymphocyte activation-promoting factor: (3) it inhibits p53 function: and (4) it relates to the proliferation and differentiation of adipocytes and cancer cells (Bucala R., FASEB J (1996)7:19-24; Bernhagen J, et al Nature 365:756-759, 1993; Calandra T, et al Nature 377:68-71, 1995).

However, excessive inflammatory response resulting from excessive production of MIF, which exhibits inflammatory effect, causes many kinds of (inflammation-associated) disorders.

There are various disorders caused by MIF. Representative disorder (disease) is known as a delayed allergy of chronic rheumatoid arthritis (type IV: cellular immune reaction). Recent years, the associated disorders have been widely apparent to cause arteriosclerosis and endometriosis, and the like. Furthermore, it is reported that the concentration of MIF in lung lavage fluid of acute respiratory distress syndrome (ARDS), urine of patients during rejection response who has received kidney transplantation, and serum of patients suffering from acute myocardial infarction, diabetes, systemic lupus erythematosus, Crohn's disease, and atopic dermatitis has risen more significantly than that of healthy person.

In addition, a set of administration of anti-MIF neutralizing antibodies apparently provides effective improvement in pathological animal models with nephritis, hepatitis, pneumonia, arthritis, and endotoxic shock (International Journal of Molecular Medicine, Volume 2, Page 17, 1998).

These studies indicate that the above-described aggravation of pathologies has been attributed to the inflammatory effect of MIF.

The following references report in detail a relationship between MIF and various disorders.

1) Makita H, et al Am J Respir Crit. Care Med 158:573-579, 1998

This reports that lipopolysaccharide (LPS) stimulus to model rats with lung disorder increases mRNA of MIF to infiltrate neutrophil and monocyte into alveoli and induce them into bronchoalveolar lavage fluid, while administration of an anti-MIF antibody before LPS administration decreases the infiltration and induction as well as inhibits breeding in lungs. This result shows that inhibition of MIF activity effectively prevents and treats lung disorders. Furthermore, it shows that the inhibition of MIF activity also effectively treats sepsis since the decrease in platelet was inhibited.

2) Kobayashi S, et al Hepatology 29:1752-1759, 1999

It is confirmed that administration of anti-MIF antibody to rat models with BCG (bacilli Calmette Guerin)-LPS-induced acute hepatitis increased survival rate and inhibited an increase of TNF-α. This indicates that inhibition of MIF activity effectively prevents and treats acute hepatitis.

3) Mikulowaska A, et al J Immunol 1585514-5517, 1997; Ichiyama H, et al Cytokine 26:187-194, 2004

It is reported that inhibition of MIF activity effectively prevents and treats rheumatoid arthritis since administration of anti-MIF antibody in experiments using type II collagen arthritis and adjuvant arthritis model animals inhibits inflammatory response.

4) Donnelly S C, et al Nat Med 3:320-323, 1997

It is confirmed that an increase in inflammatory cytokine was inhibited by administrating anti-MIF antibody to patients with acute respiratory distress syndrome (ARDS). In short, it shows that inhibition of MIF activity effectively prevents and treats acute respiratory distress syndrome (ARDS).

5) Mizue Y, et al Proc. Natl. Acad. Sci. USA 102:14410-14415, 2005

It shows that inhibition of MIF activity effectively prevents and treats bronchial asthma since administration of anti-MIF antibody effectively improved pathology of model rats with bronchial asthma.

6) Yang N, et al Mol Med 4:413-424, 1998; Lan H Y, et al J Exp Med 185:1455-1465, 1997

It shows that inhibition of MIF activity effectively prevents and treats rapidly-progressive-glomerulonephritis since administration of anti-MIF antibody effectively improved pathology of models with rapidly-progressive-glomerulonephritis.

7) Leung J C, et al Nephrol Dial Transplant 19:36-45, 2003

It shows that inhibition of MIF activity effectively prevents and treats IgA nephropathy since administration of anti-MIF antibody effectively improved pathology of models with IgA nephropathy.

As shown above, various disorders closely attribute to MIF, and therefore substances inhibiting the MIF activity are strongly desired to relieve symptoms of such disorders.

Thioredoxin is a 12 kDa multifunctional polypeptide which has oxidoreduction (Redox) activity by disulfide/ dithiol exchange reaction between two cysteine residues in an active site sequence: -Cys-Gly-Pro-Cys-, SEQ ID NO: 4 (Redox regulation of cellular activation Ann. Rev. Immunol. 1997; 15:351-369). Thioredoxin has been isolated and identified from many prokaryotes and eukaryotes since it was isolated from *Escherichia coli* as an important enzyme to synthesize hydrogen ion donor of ribonucleotide reductase and deoxyribonucleotide.

Adult T-cell leukemia derived factor (ADF) is a human thioredoxin which was firstly identified by the inventors of the present invention as an IL-2 receptor inducing factor produced by T-lymphocyte infected with HTLV-1.

Intracellular thioredoxin plays an important role in radical scavenging and controlling transcription factors related to redox, such as activator protein-1 (AP-1) and nuclear factor-kappa B (NF-κB) (AP-1 transcriptional activity is regulated by a direct association between thioredoxin and Ref-1 PNAS. 1997; 94:3633-3638).

Human thioredoxin controls signal transduction of p38 mitogen activating protein kinase (MAPK) and apoptosis signal regulating kinase-1 (ASK-1).

The inventors of the present invention reported that thioredoxin released extracellularly shows cytokine effect or chemokine effect (Circulating thioredoxin suppresses lipopolysaccharide-induced neutrophil chemotaxis PNAS. 2001; 98:15143-15148), and that extracellular TRX also moves into cells (Redox-sensing release of thioredoxin from T lymphocytes with negative feedback loops J. Immunol. 2004; 172:442-448).

However, no report has yet shown a relationship between MIF and thioredoxin and a method for screening substances related to MIF.

SUMMARY OF INVENTION

The present invention is to make it clear that thioredoxin bonds with MIF, and provide a screening method for selecting a substance which strengthens the bond between thioredoxin and MIF. The present invention further relates to a composition comprising the substance chosen in the method thereof, and a binding substance.

As a result of extensive research, the present inventors found that a polypeptide of thioredoxin family (TRXs) bonds directly with MIF, concluded that TRXs is useful to screen substances affecting the bond between TRXs and MIF, and completed the present invention.

One embodiment of the present invention is related to a screening method for selecting a test substance which strengthens a bond between a polypeptide of a thioredoxin family and a macrophage migration inhibition factor, comprising: mixing a test substance with at least one binding substance selected from following (1) to (4); (1) a polypeptide belonging to the thioredoxin family, (2) a protein having an amino acid sequence of the polypeptide belonging to the thioredoxin family in which one or more amino acid is deleted, replaced or added, and having an equivalent activity to the polypeptide of the thioredoxin family, (3) a gene coding (1), (4) a gene coding (2); bonding the binding substance to the macrophage migration inhibition factor; and monitoring the bond state between the binding substance and the macrophage migration inhibition factor.

Another embodiment of the present invention is related to the screening method, wherein the monitoring of the bond state between the binding substance and the macrophage migration inhibition factor is performed with a molecular interaction analysis.

Yet another embodiment of the present invention is related to a composition for strengthening a bond between a polypeptide of a thioredoxin family and a macrophage migration inhibition factor, comprising at least one selected from nitrosoglutathione or prostaglandin I2.

Yet another embodiment of the present invention is related to a binding substance which bonds directly with a migration inhibition factor, comprising at least one selected from following (1) to (4); (1) a polypeptide belonging to a thioredoxin family, (2) a protein having an amino acid sequence of the polypeptide belonging to the thioredoxin family in which one or more amino acid is deleted, replaced or added, and having an equivalent activity to the polypeptide of the thioredoxin family, (3) a gene coding (1), (4) a gene coding (2).

Yet another embodiment of the present invention is related to the binding substance, wherein the binding substance is a polypeptides having any one of -Cys-Gly-Pro-Cys- (SEQ ID NO: 4), -Cys-Pro-Tyr-Cys- (SEQ ID NO: 5), -Cys-Pro-His-Cys- (SEQ ID NO: 6) or -Cys-Pro-Pro-Cys- (SEQ ID NO: 7) in an active center.

The present invention effectively works for screening a test substance which strengthens a bond between thioredoxin and macrophage migration inhibition factor. The screened test substance further enhances the inhibition of the activity of macrophage migration inhibition factor resulting from the binding substance (polypeptide of thioredoxin family and the like).

The molecular interaction analysis allows to monitor the intermolecular bond state in real time.

Nitrosoglutathione and prostaglandin I2 enable to certainly strengthen the bond between the polypeptide of the thioredoxin family and macrophage migration inhibitory factor.

The polypeptide of the thioredoxin family has any one of -Cys-Gly-Pro-Cys- (SEQ ID NO: 4), -Cys-Pro-Tyr-Cys- (SEQ ID NO: 5), -Cys-Pro-His-Cys- (SEQ ID NO: 6) or -Cys-Pro-Pro-Cys- (SEQ ID NO: 7) in the active center to certainly bond with macrophage migration inhibitory factor.

BRIEF DESCRIPTION OF THE DRAWINGS

FIG. 1 shows the bond between TRX and MIF in the cell.

DETAILED DESCRIPTION OF THE INVENTION

Figure 2:
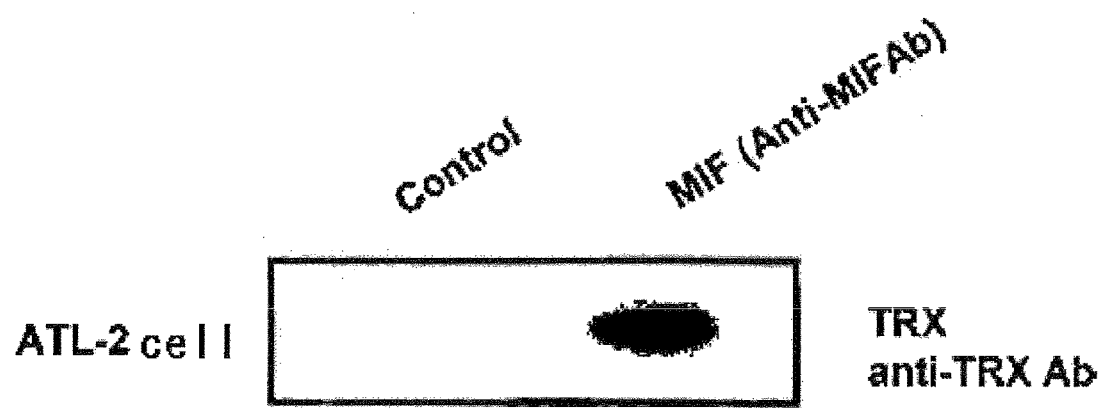
FIG. 2 shows the bond between TRX and MIF outside the cell.

As a result of extensive research, the present inventors revealed that a polypeptide of a thioredoxin family (TRXs)

bonds directly with a macrophage migration inhibitory factor (MIF) having inflammatory effect, as its new function.

Based on the study, the inventors conclude that TRXs is useful to select the substances affecting the bond between MIF and TRXs, and the present invention is completed.

Hereinafter, an embodiment of the screening method according to the present invention will be explained in detail.

The screening method of the present invention selects a substance to strengthen a bond between TRXs and MIF.

Specifically, the method comprises following steps (a) to (c):
(a) mixing a binding substance such as TRXs (to be described in detail below) with a test substance;
(b) bonding the binding substance mixed with the test substance to MIF;
(c) monitoring a bond state between the binding substance mixed with test substance and MIF to be compared to a bond state between a sole binding substance (without being mixed with the test substance) and MIF.

As a result of the analysis, if the bond between the binding substance mixed with test substance and MIF is stronger than the bond between a sole binding substance (without being mixed with the test substance) and MIF, the test substance strengthens the bond between the binding substance and MIF.

The binding substance (such as TRXs) bonds with MIF, and inhibits MIF activity as a MIF inhibitor. The selected substance which strengthens the bond between the binding substance and MIF remarkably exhibits the effect of the binding substance as a MIF inhibitor.

Various peptides, lipids, and sugar chains may be used for the test substance.

It was confirmed with the screening method of the present invention that Nitrosoglutathione and prostaglandin I2 strengthen the bond between TRXs and MIF. Therefore, the composition comprising at least one selected from nitrosoglutathione or prostaglandin I2 is preferably used to strengthen the bond between TRXs and MIF.

Also, prostaglandin J2(PGJ2) family, hyaluronan, S_Nitrosylation, Glutathionylation, and the like may be used.

Molecular interaction analysis (Biacore) utilizing surface plasmon resonance (SPR) phenomenon may be used for the method in order to confirm the bond state between the binding substance and MIF. This anaysis enables to monitor the molecular interaction in real time without any labels.

For the molecular interaction analysis, MIF is immobilized in a sensor chip as a ligand, and the mixture of the binding substance (such as TRXs) and the test substance is used as an analyte to analyze the bond state (interaction) between the binding substance mixed with the test substance and MIF. Thus, the analysis result is compared with the bond state between the binding substance without being mixed with the test substance and MIF to screen the test substance.

[TRXs]

Hereinafter, the binding substance of the present invention will be explained.

The binding substance of the present invention indicates following (1) to (4). The following (1) to (4) may be used alone or in combination:
(1) a polypeptide of a thioredoxin family (TRXs);
(2) a polypeptide having TRXs amino acid sequence in which one or more amino acid is deleted, replaced or added, and having the equivalent activity to TRXs;
(3) a gene coding (1);
(4) a gene coding (2).

The equivalent activity to the polypeptide belonging to the thioredoxin family (TRXs) means the activity which enables to bond directly with MIF.

TRXs is polypeptides having oxidoreduction activity of dithiol or disulfide bond, and originally existing in cellular organisms (See JP2002-179588).

TRXs of the present invention includes not only natural polypeptides extracted from animals including human, plants, *Escherichia coli*, yeast, and the like, but also polypeptides extracted from yeast or *Escherichia coli* by gene recombination or polypeptides produced by the chemical synthesis. However, polypeptides originally derived from human, polypeptides produced by gene recombination in *Escherichia coli* or yeast based on the human origin polypeptide, or synthetic peptide having the same or analogous sequence as the human origin polypeptide may be preferably used in view of less effect on the biological body.

TRXs has an active site including cysteine residues (-Cys-X1-X2-Cys-: X1 and X2 represent any amino acid residue, respectively, and may be same or different), and it is a molecular group having a similar three-dimensional structure. In addition to the above, TRXs of the present invention may include TRXs in which partial amino acid is deleted or replaced as well as TRXs fused with other amino acid or peptide, as far as keeping oxidoreduction activity of dithiol or disulfide bond.

For specific examples of the active site, -Cys-Gly-Pro-Cys- (SEQ ID NO: 4), Cys-Pro-Tyr-Cys- (SEQ ID NO: 5), -Cys-Pro-His-Cys- (SEQ ID NO: 6) and Cys-Pro-Pro-Cys- (SEQ ID NO: 7) are exampled. Among them, -Cys-Gly-Pro-Cys- (SEQ ID NO: 4) is preferably used because the sequence is well preserved over species, and experimental results of mouse model are reliably applied to human.

For TRXs, in particular, thioredoxin (TRX) and glutaredoxin of which active sites are -Cys-Gly-Pro-Cys- (SEP ID NO: 4) are used.

Thioredoxin (TRX) may be derived from human, *Escherichia coli*, or yeast, and glutaredoxin may be derived from human or *Escherichia coli*.

Here, human thioredoxin derived from human (hTRX) is a polypeptide consisting of 105 amino acid shown in the sequence number 1. The base sequence of hTRX is shown in the sequence number 2. The specific methods for extracting TRXs from human cells are shown below.
(A) a method for extracting TRXs from human-derived cell strains (See JP1-85097)
(B) a method with gene recombination (See JP1-85097)
(C) a method with peptide synthesis (See JP5-139992)

A modified TRX based on the human thioredoxin of the sequence number 1 produced by known genetic engineering procedures may be used, as far as keeping the ability for bonding directly with MIF.

The modified TRX may include TRX in which one or more amino acid except at 32 and 35 positions of the sequence number 1, preferably except at 32 to 35 positions, is replaced, deleted, added or inserted.

Polypeptide belonging to the above thioredoxin family (TRXs) may be used in single kind of peptide or more than two kinds of peptides.

Further, the polypeptide described in (1) and (2) in cells may be produced to use the coding genes described in (3) and (4).

[Macrophage Migration Inhibitory Factor (MIF)]

Next, MIF used in the screening method of the present invention will be explained below.

MIF exists in various animal species including humans. It is a 12.3-kDa protein consisting of 115 amino acid residues shown in the sequence number 3, and has a redox active domain: Cys-X—X-Cys- motif (X may be any amino acid) in the molecule. Therefore, it belongs to the thioredoxin family.

MIF is expressed in not only lymphocytes but also various organs such as brain and kidney. It is strongly expressed in uriniferous tubular epithelial cells in the kidney, and also expressed in actively proliferating basal membrane cells in skin and cornea.

MIF-expression cells and tissues may include T cells, monocytes/macrophages, dendritic cells, mesangial cells, uriniferous tubular epithelial cells, corneal epithelial cells, hepatocytes, ova, Sertoli cells, keratinocytes, osteoblasts, synovial cells, adipocytes, astrocytes, cancer cells, mucosa and pituitary.

The present invention is not to be limited in scope by the followings. The binding substance (such as TRXs) bonds directly with MIF having inflammatory effect so as to reduce MIF activity and inhibit the inflammation caused by MIF (and fibrosis caused by the inflammation). For details, it is considered that the binding substance (such as TRXs) bonds directly with the redox active domain of MIF in order to inhibit the MIF activity.

The binding substance (such as TRXs) inhibits the cell internalization (incorporation) of MIF so as to reduce the inflammation caused by MIF (and fibrosis caused by the inflammation).

The screening method of the present invention allows to select the substance which strengthens the bond between the binding substance (such as TRXs) and MIF. Therefore, the screening method of the present invention enables to seek the substance which further strengthens the effect of the binding substance (such as TRXs) on MIF.

Hereinafter, the present invention will be specifically explained referring to the examples below, but it is not limited to these examples.

Example 1

Confirmatory Experiment of the Bond Between TRX and MIF in Cells

The bonds between TRX and MIF in ATL2 cells and HL60 cells were confirmed with an immunoprecipitation method (to be described in detail below).
[Materials]
ATL2 cells; human adult T-cell leukemia cell strain (See Publication JP62-19532, Tagaya, Y., Y. Maeda, A. Mitsui, N. Kondo, H. Matsui, J. Hamuro, N. Brown, K. Arai, T. Yokota, H. Wakasugi, et al 1989. EMBO J. 8:75)
HL60 cells; human acutepromyelocytic leukemia cell strain (provided by Dr. YODOI Junji, Institute for Virus Research in Kyoto University)
Protein G Sepharose 4 Fast Flow; (GE Healthcare Bio-Sciences Ltd.)
Anti TRX antibody (ADF 11 antibody); (Redox Bioscience Inc.)
Anti MIF antibody; (Santa Cruz Biotechnology, Inc.)
Anti Rabbit antibody; (Upstate, Inc.)
[Method]
The cells were cultured with RPMI 1640 (SIGMA Inc.) medium containing 10% FCS, 100 U/ml penicillin and 100 μg/ml streptomycin in a 175 cm² flask.

$1 \times 10^{7 \sim 8}$/cell of the cells were collected and centrifugated at 1,000 rpm and 4° C. for 15 minutes. The obtained precipitation was dissolved with lysis buffer and left on the ice for 30 minutes.

The solution was centrifugated at 1,000 rpm and 4° C. for 15 minutes. The obtained supernatant was used for the immunoprecipitation experiment. The concentration of the protein was measured with DC protein assay kit (BIO RAD Inc.).

20 μl Protein G Sepharose and 500 μg of the cell solution were added to a microtube, and phosphate buffer was used to adjust the amount to 1 ml. The obtained solution was reacted at 4° C. for 3 hours with a small rotary incubator. The cell solution was centrifugated at 15,000 rpm and 4° C. for 2 minutes. The obtained supernatant was added to a new microtube, and 20 μl Protein G Sepharose and 4 μg/ml anti MIF antibody were also added thereto.

For a control, anti Rabbit antibody was used instead of the anti MIF antibody.

The reaction was carried out with a small rotary incubator at 4° C. for overnight. The reaction solution was centrifugated at 15,000 rpm and 4° C. for 2 minutes. The precipitation was washed with washing buffer (50 mM Tris-HCl (pH7.5), 150 mM NaCl, 0.1% NP40).

The precipitation added to SDS-PAGE sample buffer was provided to 15% SDS PAGE gel. After the cataphoresis, a Western blotting was performed (with the anti TRX antibody) (ADF11 antibody) to confirm the bond (FIG. 1).

FIG. 1 shows that TRX bonds directly with MIF in both ATL2 cells and HL60 cells.

Example 2

Experiment of the Bond Between TRX and MIF Outside Cells

The bond between TRX and MIF outside ATL2 cells was confirmed with an immunoprecipitation method.
[Materials]
ATL2 cells; human adult T-cell leukemia cell strain
(See Publication JP62-19532, Tagaya, Y., Y. Maeda, A. Mitsui, N. Kondo, H. Matsui, J. Hamuro, N. Brown, K. Arai, T. Yokota, H. Wakasugi, et al 1989. EMBO J. 8:75)
Protein G Sepharose 4 Fast Flow; (GE Healthcare Bio-Sciences Ltd.)
Anti TRX antibody (ADF 11 antibody); (Redox Bioscience Inc.)
Anti MIF antibody; (Santa Cruz Biotechnology, Inc.)
Anti Rabbit antibody; (Upstate, Inc.)
Amicon ultra-4; (Millipore, Inc.)
[Method]
$1 \times 10^5$/cell of the ATL2 cells were cultured with RPMI 1640 (SIGMA Inc.) medium containing 100 U/ml penicillin and 100 μg/ml streptomycin in a 175 cm² flask for 3 days. Then, the medium was collected and centrifugated at 10,000 rpm and 4° C. for 15 minutes. Then, FCS was added to the obtained supernatant to adjust the final concentration to 10%, and the solution was concentrated with Amicon ultra-4. The obtained concentrated-solution was used for the immunoprecipitation experiment. 20 μl Protein G Sepharose and 30 μl of the culture supernatant were added to a microtube, and phosphate buffer was used to adjust the amount to 1 ml. The obtained solution was reacted at 4° C. for 3 hours with a small rotary incubator. The cell solution was centrifugated at 15,000 rpm and 4° C. for 2 minutes. The obtained supernatant was added to a new microtube, and 20 μl Protein G Sepharose and 4 μg/ml of the anti MIF antibody were also added thereto.

For a control, anti Rabbit antibody was used instead of the anti MIF antibody.

The reaction was carried out with a small rotary incubator at 4° C. for overnight. The reaction solution was centrifugated at 15,000 rpm and 4° C. for 2 minutes. The precipitation was washed with washing buffer (50 mM Tris-HCl (pH7.5), 150 mM NaCl, 0.1% NP40).

The precipitation added to SDS-PAGE sample buffer was provided to 15% SDS PAGE gel. After the cataphoresis, a Western blotting was performed (with the anti TRX antibody) (ADF11 antibody) to confirm the bond (FIG. 2).

FIG. 2 shows that TRX bonds directly with MIF outside ATL2 cells.

Example 3

Confirmatory Experiment of TRX Inhibiting the Cell Internalization of MIF

MIF is internalized (incorporated) into cells by the autocrine or paracrine action to induce the production of inflammatory cytokine TNF-alpha($\alpha$) or IL-1. Thus, the effects of TRX on the cell internalization of MIF were examined to clarify the inflammation response control mechanism.
[Materials]
ATL2 Cells; Human Adult T-Cell Leukemia Cell Strain
Recombinant MIF (rMIF); His-tagged recombinant MIF was expressed in *Escherichia coli* by using expression vector pQE30 (QIAGEN Inc.), and column-purified with MagneHis™ Protein Purification System (Promega Corp.).
Recombinant TRX (rTRX) (Ajinomoto Co., Inc.)
Anti His-tagged antibody (Promega Corp.).
[Method]
ATL2 cells were cultured with RPMI 1640 medium containing 10% FCS, 100 U/ml penicillin and 100 µg/ml streptomycin in a 75 cm$^2$ flask.

$1\times10^6$/cell of ATL2 cells were added to a 24 well plate. rTRX having the final concentration of 0 to 250 µg/ml and 25 µg/ml rMIF were also added thereto, and cultured under the condition of 0.5% $CO_2$ at 37° C. for 24 hours.

After cells were collected, the precipitation was mixed with SDS-PAGE sample buffer, and then electrophoresed on a 15% SDS-PAGE gel. After the electrocataphoresis, a Western blotting was performed to detect MIF internalized in the cells with anti His-tagged antibody. The change of the band by the Western blotting was analyzed with a densitometer. The result is shown in FIG. 3.

Figure 3:
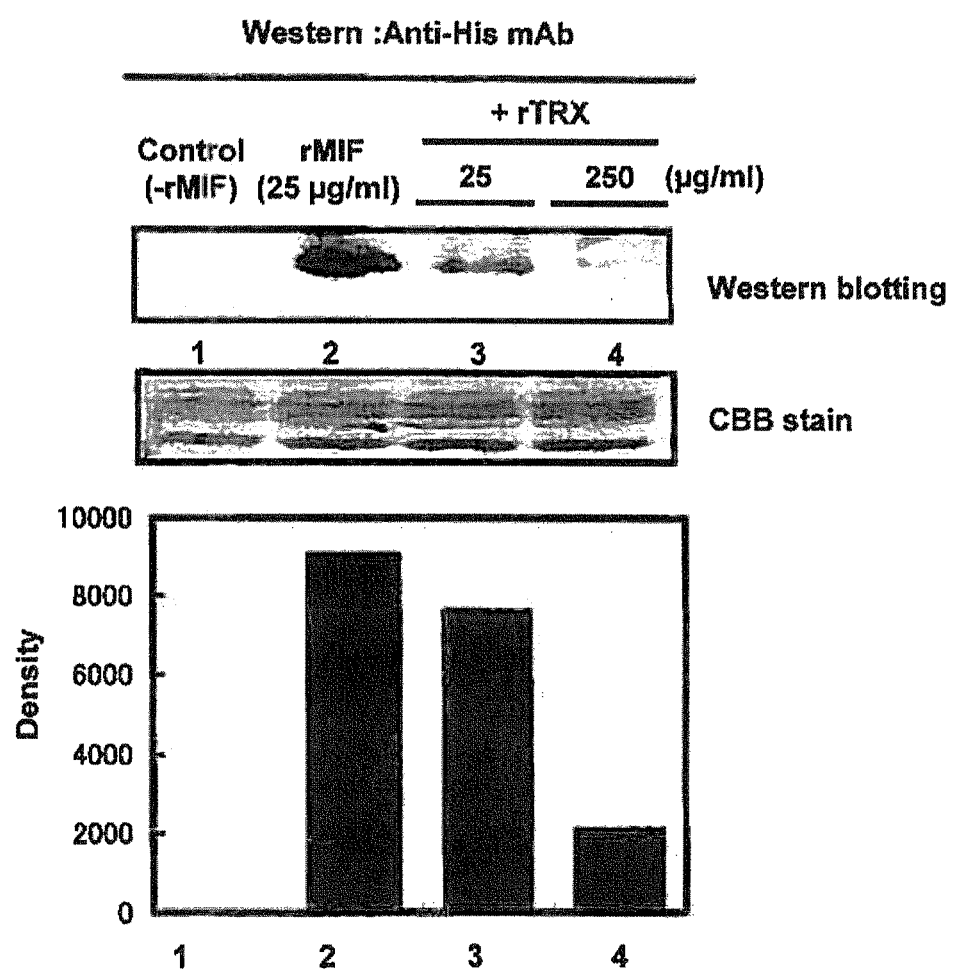
FIG. 3 shows the inhibition of the cell internalization of MIF by TRX.

FIG. 3 shows that TRX inhibits the internalization of MIF into the ATL2 cells. This means that TRX inhibits the internalization of MIF into cells so as to reduce the inflammatory response.

Example 4

Confirmatory Experiment of TRX's Inhibition of MIF Activity

TRX's inhibition of MIF activity was confirmed by measuring a concentration of inflammatory cytokine TNF-$\alpha$ (to be described in detail below).
[Materials]
RAW 264.7 cells; mouse-derived macrophage cell strains (provided by Dr. ISHII Yasuyuki, RIKEN, Research Center for Allergy and Immunology)
Recombinant MIF (rMIF); (ATGEN CO., LTD.)
Recombinant TRX (rTRX); (Ajinomoto Co., Inc.)
Lipopolysaccharide (LPS); (SIGMA, Inc.)
TNF-$\alpha$ ELISA kit; (R&D SYSTEMS, Inc.)
[Method]
RAW 264.7 cells were cultured with RPMI 1640 medium containing 10% FCS, 100 U/ml penicillin and 100 µg/ml streptomycin in a 75 cm$^2$ flask.

RAW 264.7 cells were added to a 24 well plate ($1\times10^6$/cell). MIF having a final concentration of 10 ng/ml and 0 to 500 ng/ml TRX were also added thereto, and left under the condition of 5% $CO_2$ at 37° C. for 4 hours.

Further, 100 ng/ml of LPS was added to the plate (described as LPS (+)), and the plate was left under the condition of 5% $CO_2$ at 37° C. for 4 hours. Then, the medium was collected.

Amount of the generated TNF-alpha ($\alpha$) was measured with Duo Set ELISA Development system mouse TNF-$\alpha$ kit.

The measuring method was based on the protocol attached to the kit. The measurement result is shown in FIG. 4.

Figure 4:
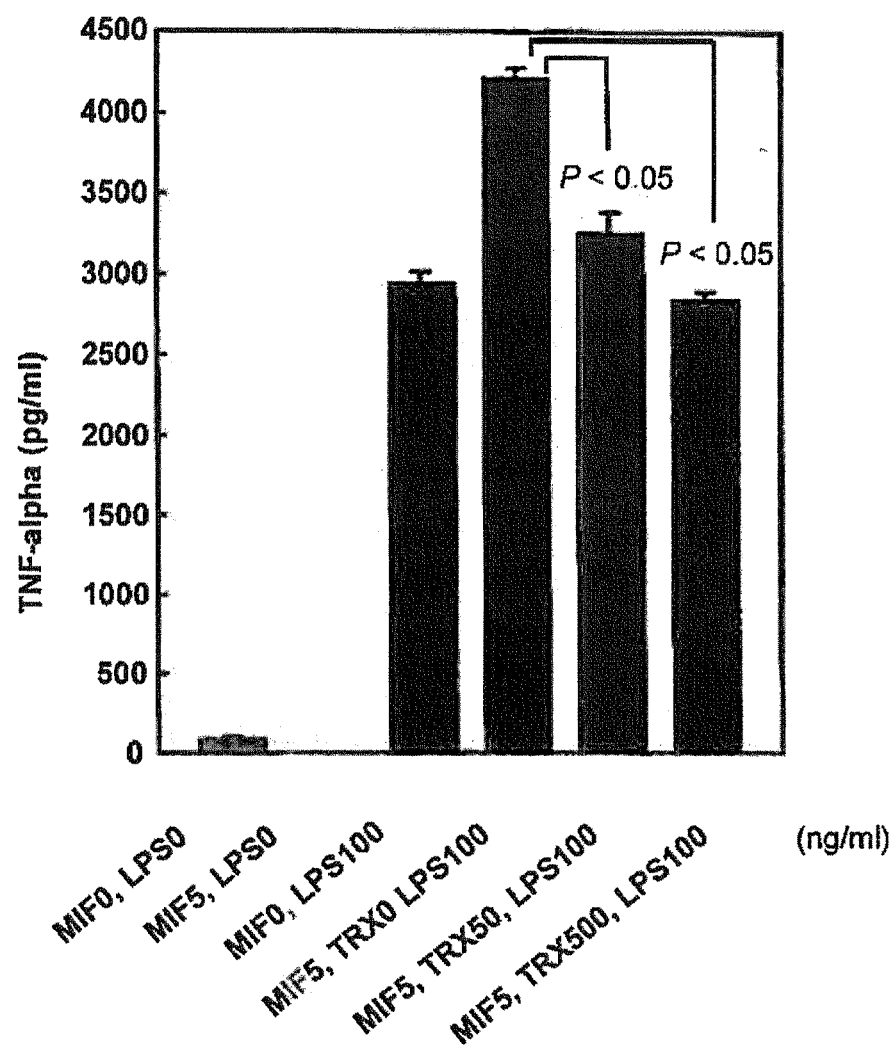
FIG. 4 shows the inhibition of MIF activity by TRX by referring to the concentration of TNF-alpha ([α]).

FIG. 4 shows that rTRX inhibits the activity of rMIF depending on the concentration of rTRX, and inhibits the production of MIF-derived TNF-alpha, which is an inflammatory cytokine.

From the results shown in the above examples 1 to 3, it is found that TRX bonds directly with MIF to inhibit the transfer of MIF into cells.

The result of the example 4 shows that the polypeptide of the thioredoxin family inhibits the internalization of MIF into cells. This results in inhibiting the production of TNF-alpha and the inflammatory response.

Thus, TRX is effective for widely various disorders caused by MIF.

Example 5

Confirmatory Experiment 1 of the Bond Between TRX and MIF

The bond between TRX and MIF was confirmed with a molecular interaction analysis (Biacore) (hereinafter, referred to as "molecular interaction analysis") utilizing surface plasmon resonance (SPR) phenomenon.
[Materials]
Recombinant MIF (rMIF); His-tagged rMIF was expressed in *Escherichia coli* by using expression vector pQE30 (QIAGEN Inc.), and column-purified with MagneHis™ Protein Purification System (Promega Corp.).
Recombinant TRX (rTRX); His-tagged rTRX was expressed in *Escherichia coli* by using expression vector pQE80L (QIAGEN Inc.), and column-purified with MagneHis™ Protein Purification System (Promega Corp.).
Anti His-tagged antibody; (Promega Corp.)
BIAcore2000; (using a CM5 sensor chip); (Biacore, Inc.)
[Method]
rMIF was immobilized in a CM5 sensor chip as a ligand. The ligand was adjusted to include MIF less or equal to 200 nM by using running buffer, 10 mM HEPES (pH7.4), 150 mM NaCl, 3 mM EDTA and 0.005% Tween 20.

Then, rTRX was used as an analyte to analyze the interaction between rTRX and rMIF. The concentration of rTRX was changed to 2 µM, 4 µM, 6 µM, 8 µM, 10 µM and 12 µM for the analysis.

Figure 5:
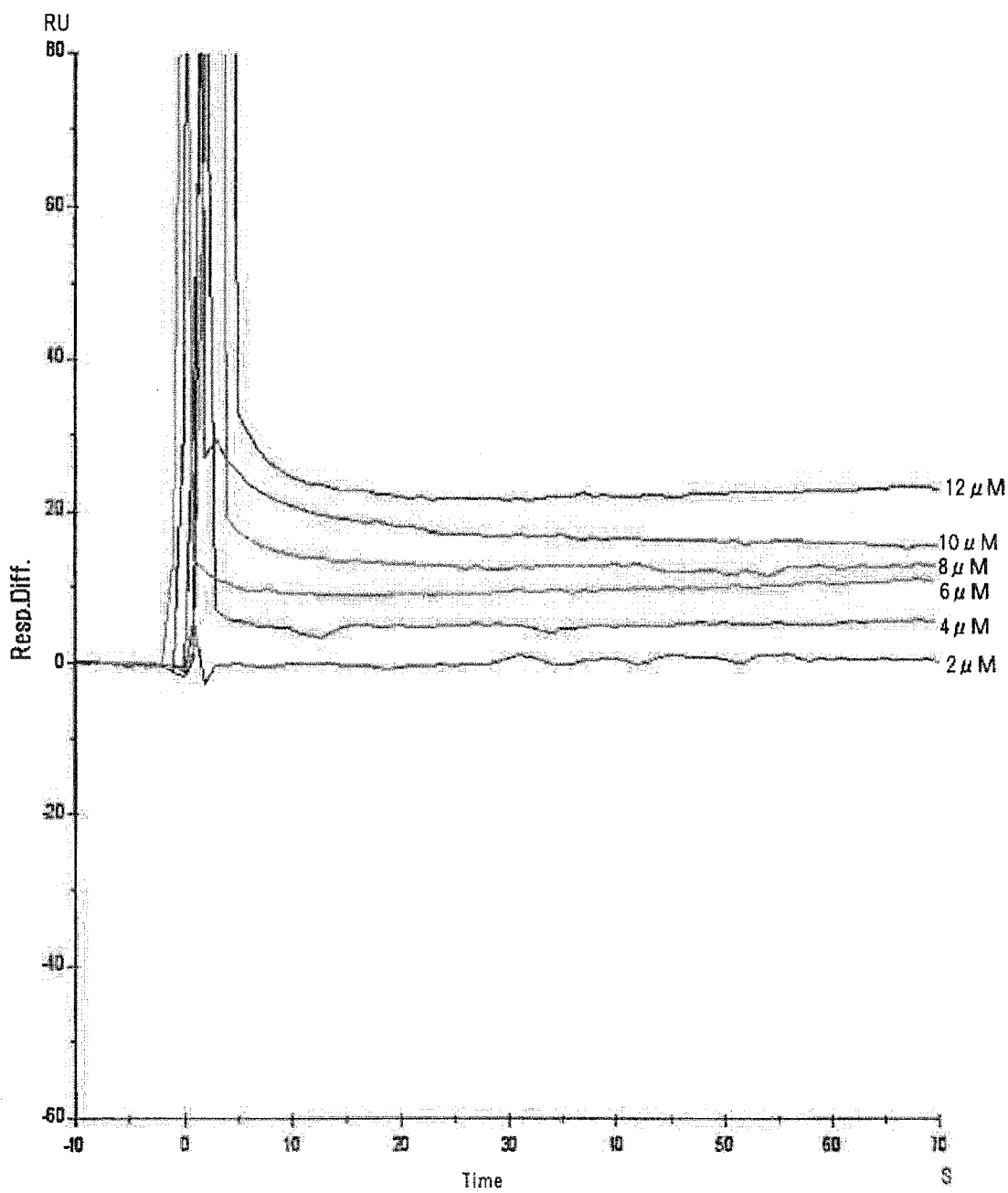
FIG. 5 shows the molecular interaction analysis result of the bond between TRX and MIF.

FIG. 5 shows the molecular interaction analysis result of Example 5.

As shown in FIG. 5, the surface plasmon resonance phenomenon increases depending on the concentration of rTRX. This shows that the bond between rTRX and rMIF is concentration-dependent.

Also, the experiment with the same method for using a sensor chip NTA (Ni-Histag) showed the same result.

Example 6

Confirmatory Experiment 2 of the Bond Between TRX and MIF

It was confirmed with a molecular interaction analysis whether the cysteine residues at 32 and 35 positions (the active site of TRX) affect the bond between TRX and MIF or not.

[Materials]

rWT TRX; (same as the rTRX of Example 5)

rDM TRX; (the rTRX of Example 5 in which the cysteine residues at 32 and 35 positions were converted to serine)

rC35S TRX; (the rTRX of Example 5 in which the cysteine residue at 35 position of the rTRX was converted to serine)

rMIF; (same as the rMIF of Example 5)

BIAcore2000; (CM5 sensor chip)

[Method]

rMIF was immobilized in a CM5 sensor chip as a ligand, wherein the concentration of rMIF was adjusted to less than or equal to 200 nM.

Then, rWT TRX, rDM TRX and rC35S TRX were used as analytes to analyze the interaction between these rTRX and rMIF in both oxidation and reduction states, respectively.

In the oxidation state, running buffer, 10 mM HEPES (pH7.4), 150 mM NaCl, 3 mM EDTA and 0.005% Tween 20 were used to adjust the ligand. In the reduction state, 1M DTT was used in addition to the running buffer, 10 mM HEPES (pH7.4), 150 mM NaCl, 3 mM EDTA and 0.005% Tween 20 to adjust the ligand.

Figure 6:
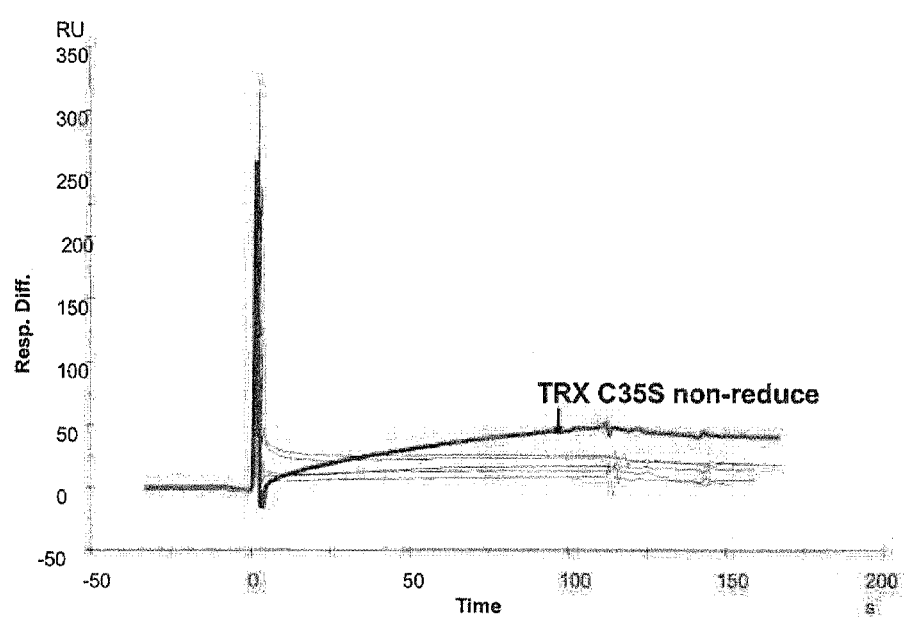
FIG. 6 shows the molecular interaction analysis result of the bond between TRX and MIF.

FIG. 6 shows the result of the molecular interaction analysis of Example 6.

Tables 1 and 2 show the dissociation constant value (KD value) calculated from FIG. 6. Table 1 shows KD values of rTRX and rMIF in the oxidation state. Table 2 shows KD values of rTRX and rMIF in the reduction state.

TABLE 1

| oxidation state | KD |
|---|---|
| rWT TRX | $2.53 \times 10^{-5}$ |
| rDM TRX | $1.19 \times 10^{-5}$ |
| rC35S TRX | $3.95 \times 10^{-6}$ |

TABLE 2

| reduction state | KD |
|---|---|
| rWT TRX | $2.97 \times 10^{-5}$ |
| rDM TRX | $1.66 \times 10^{-5}$ |
| rC35S TRX | $4.32 \times 10^{-4}$ |

As shown in FIG. 6 and Tables 1 and 2, it was confirmed that all of rWT TRX, rDM TRX and rC35S TRX bonded directly with rMIF. In particular, the bond between rMIF and rC35S TRX was stronger than the bond between rWT TRX or rDM TRX and MIF.

It was also confirmed that rWT TRX and rDM TRX showed almost no changes in the dissociation constant values in both the oxidation state and the reduction state, and rC35S TRX showed the strong bond with rMIF in the oxidation state.

This shows that the TRX active site Cys-Gly-Pro-Cys, SEQ ID NO: 4 (at 32 to 35 positions) includes a part with redox dependency and a part without redox dependency.

Example 7

Screening Experiment for a Molecule Affecting the Bond Between TRX and MIF

For several test substances, it was confirmed with a molecular interaction analysis whether they strengthened the bond between TRX and MIF or not.

[Materials]

rTRX; (same as the rTRX of Example 5)

rMIF; (same as the rMIF of Example 5)

BIAcore2000; (CM5 sensor chip)

(Test Material)

N-acetylglucosamine

Nitrosoglutathione

Prostaglandin I2

[Method]

rMIF was immobilized in a CM5 sensor chip as a ligand. The ligand was adjusted to have the rMIF concentration of less or equal to 200 nM by using running buffer, 10 mM HEPES (pH7.4), 150 mM NaCl, 3 mM EDTA and 0.005% Tween 20.

Then, N-acetylglucosamine, Nitrosoglutathione and Prostaglandin I2 were mixed with rTRX, respectively, to form three types of analytes.

In each analyte, the concentration of rTRX was 5 µM and the concentration of the test substance was 500 µM. For Prostaglandin I2, the analyte having its concentration of 5 µM was also analyzed.

Figure 7:
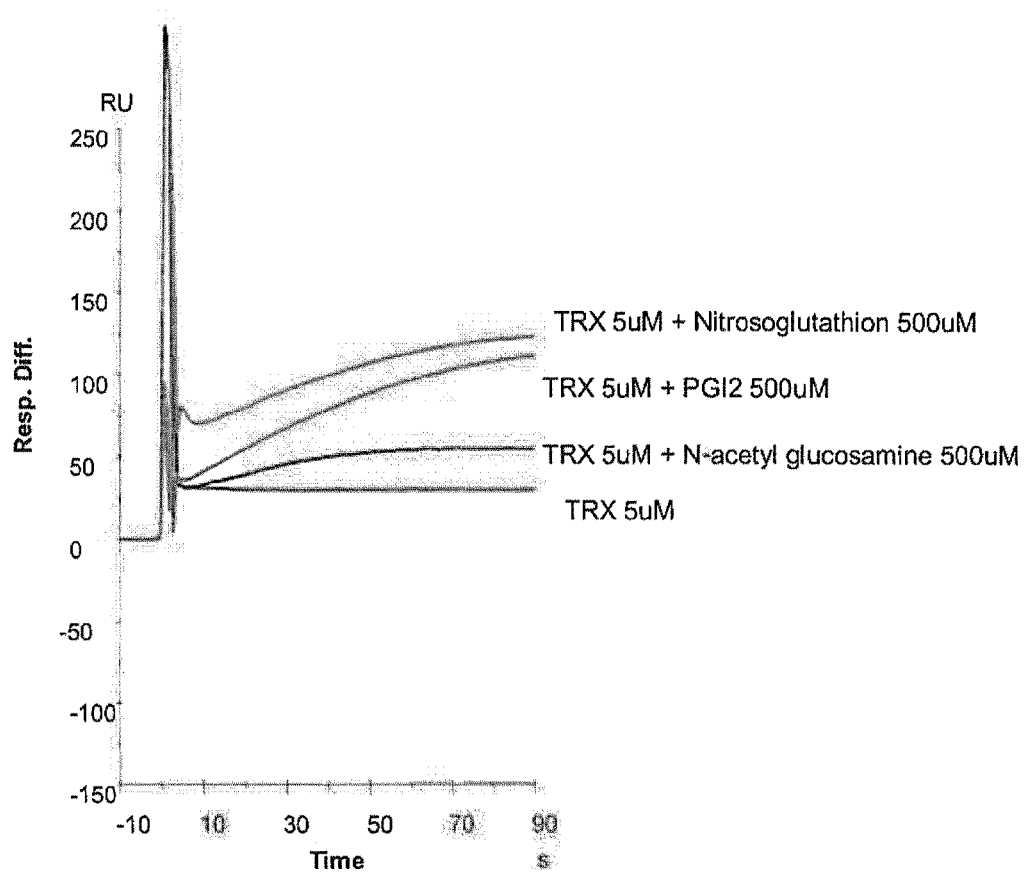
FIG. 7 shows the molecular interaction analysis result by using the mixtures of TRX and three test substances, respectively, as analytes.

FIG. 7 shows the molecular interaction analysis result by using analytes produced by mixing the three types of test substances with rTRX, respectively. FIG. 7 also shows the molecular interaction analysis result by using only rTRX (5 µM).

Figure 8:
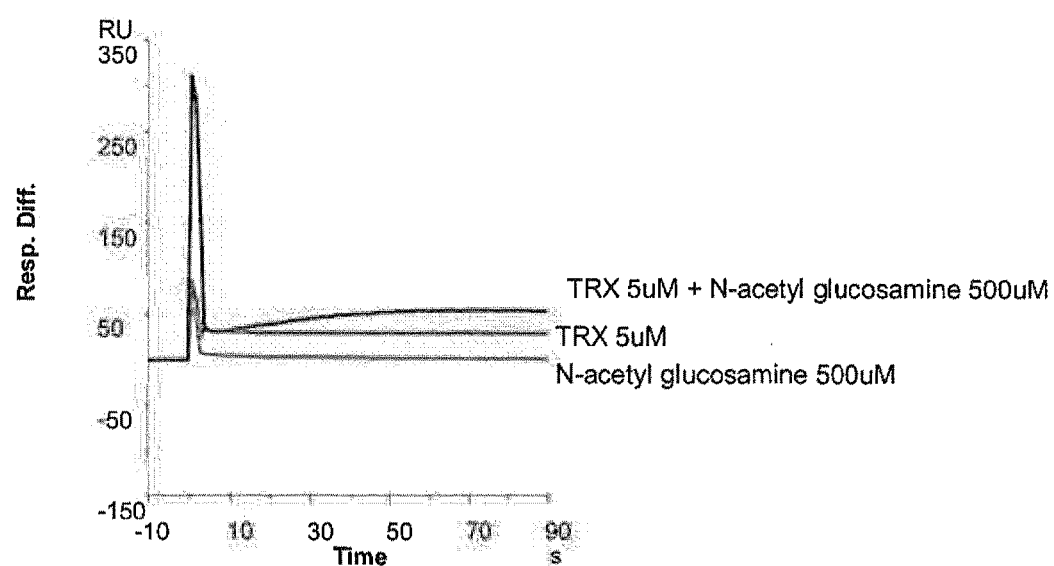
FIG. 8 shows the molecular interaction analysis result by using N-acetylglucosamine as a test substance.

FIG. 8 shows the molecular interaction analysis result by using N-acetylglucosamine as a test substance. FIG. 8 also shows the molecular interaction analysis results by using only rTRX (5 µM) and only N-acetylglucosamine (500 µM), respectively.

Figure 9:
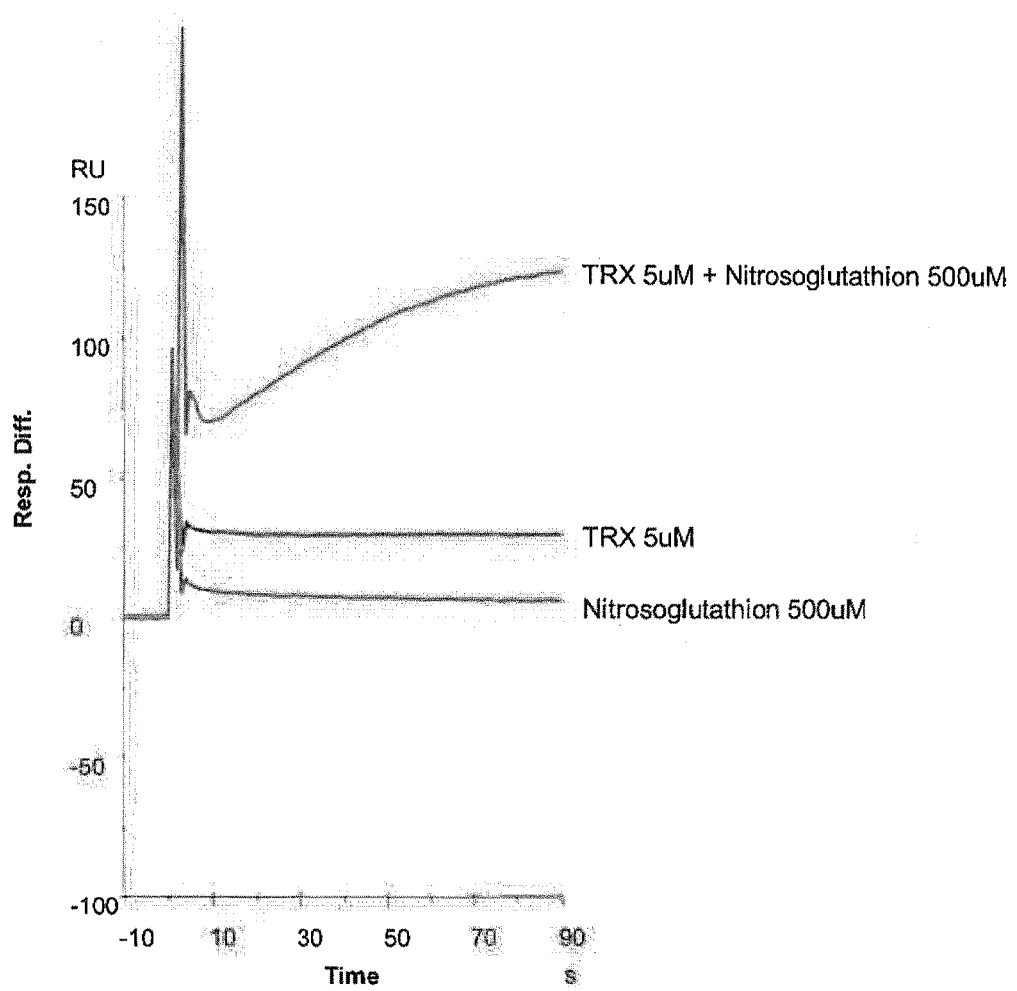
FIG. 9 shows the molecular interaction analysis result by using nitrosoglutathione as a test substance.

FIG. 9 shows the molecular interaction analysis result by using nitrosoglutathione as a test substance. FIG. 9 also shows the molecular interaction analysis results by using only rTRX (5 µM) and only nitrosoglutathione (500 µM), respectively.

Figure 10:
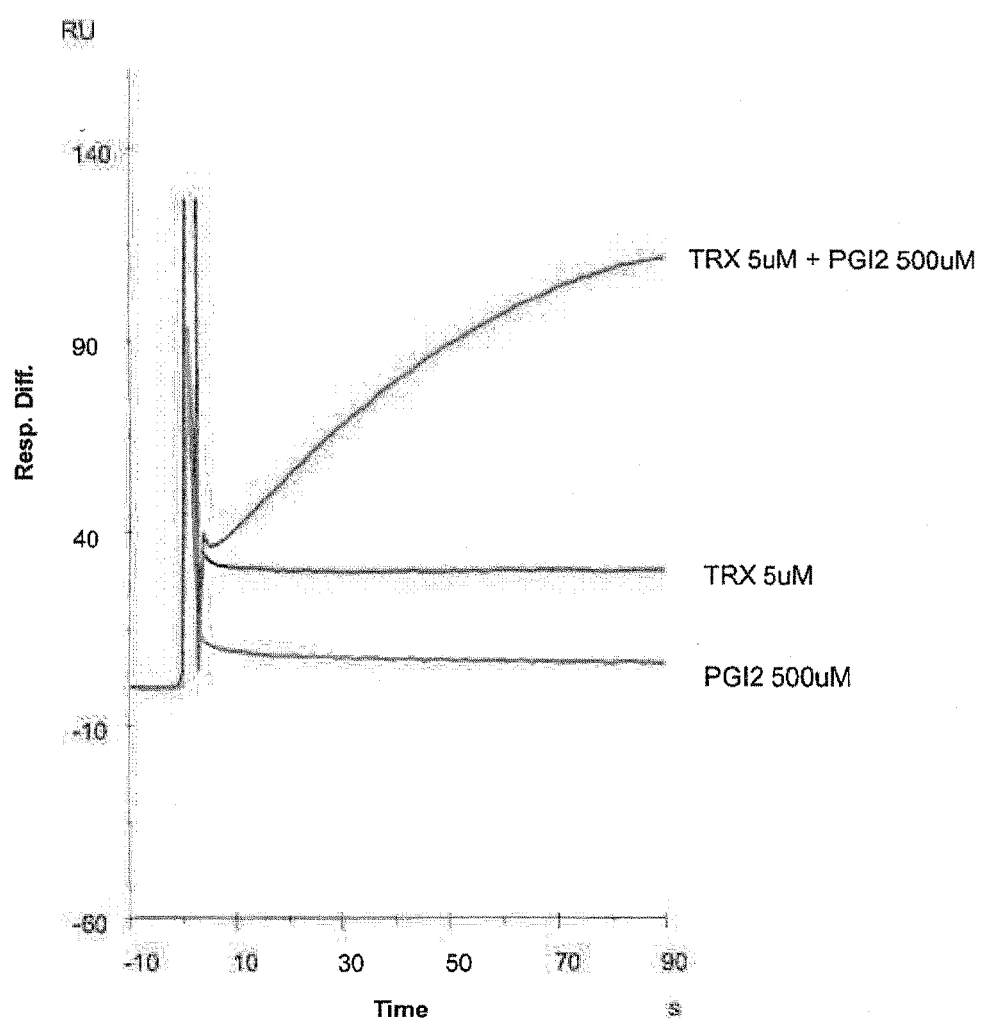
FIG. 10 shows the molecular interaction analysis result by using prostaglandin I2 as a test substance.

FIG. 10 shows the molecular interaction analysis result by using prostaglandin I2 as a test substance. FIG. 10 also shows the molecular interaction analysis results by using only rTRX (5 µM) and only prostaglandin I2 (500 µM), respectively.

Figure 11:
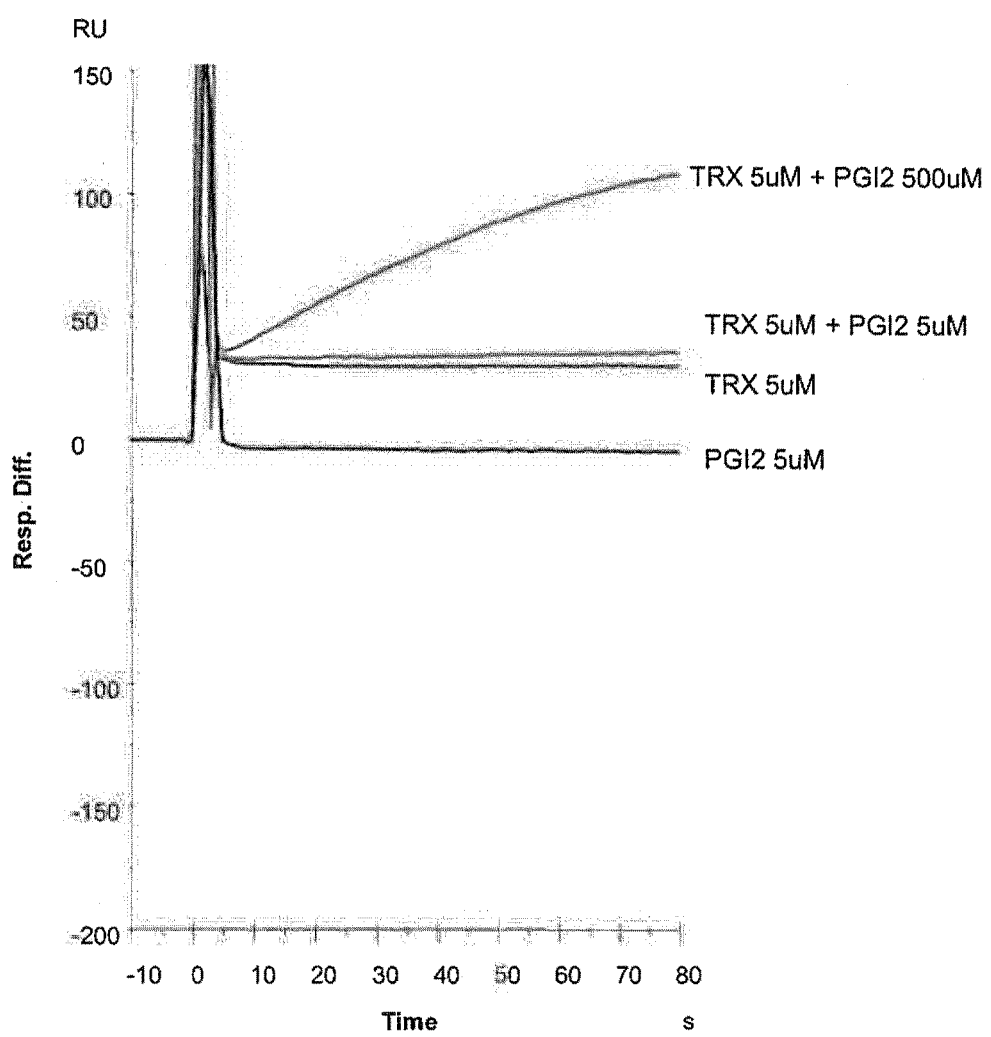
FIG. 11 shows the molecular interaction analysis result by using prostaglandin I2 as a test substance.

FIG. 11 shows the molecular interaction analysis result by using an analyte mixing rTRX and prostaglandin I2 as a test substance, wherein the concentration of the prostaglandin I2 is 5 µM and 500 µM.

As shown in FIGS. 7 to 11, it was confirmed that Nitrosoglutathione and Prostaglandin I2 were mixed with rTRX, respectively, to remarkably strengthen the bond between rTRX and rMIF.

This shows that Nitrosoglutathione and Prostaglandin I2 are the substances which strengthen the bond between TRXs and MIF.

As shown above, the screening method of the present invention allows to screen a substance which strengthens the bond between TRXs and MIF.

The invention claimed is:

1. A screening method for selecting a test substance which strengthens a bond between a thioredoxin protein and a macrophage migration inhibition factor, comprising:

mixing the test substance with a binding substance that is a naturally-occurring human thioredoxin protein, whose amino acid sequence is shown in SEQ ID NO: 1 and whose is -Cys-Gly-Pro-Cys (SEQ ID NO: 4), or a protein having an amino acid sequence of the polypeptide of the human thioredoxin protein in which one or both of the cysteines in the active site are mutated;

bonding the binding substance to a naturally-occurring human macrophage migration inhibition factor; and monitoring a bond state between the binding substance mixed with the test substance and the naturally-occurring human macrophage migration inhibition factor compared to a bond state between a binding substance without being mixed with the test substance and the naturally-occurring human macrophage migration inhibition factor, thereby selecting the test substance having a stronger bond with the naturally-occurring human macrophage migration inhibition factor than a bond formed by a binding substance without being mixed with the test substance.

2. The screening method according to the claim 1, wherein the monitoring of the bond state between the binding substance and the naturally-occurring human macrophage migration inhibition factor is performed with a molecular interaction analysis.

* * * * *

SEQUENCE LISTING

<160> NUMBER OF SEQ ID NOS: 7

<210> SEQ ID NO 1
<211> LENGTH: 105
<212> TYPE: PRT
<213> ORGANISM: Homo sapiens

<400> SEQUENCE: 1

Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
            20                  25                  30

Gly Pro Cys Lys Met Ile Lys Pro Phe Phe His Ser Leu Ser Glu Lys
        35                  40                  45

Tyr Ser Asn Val Ile Phe Leu Glu Val Asp Val Asp Asp Cys Gln Asp
    50                  55                  60

Val Ala Ser Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Val
            100                 105

<210> SEQ ID NO 2
<211> LENGTH: 318
<212> TYPE: DNA
<213> ORGANISM: Homo sapiens

<400> SEQUENCE: 2
atggtgaagc agatcgagag caagactgct tttcaggaag ccttggacgc tgcaggtgat      60
aaacttgtag tagttgactt ctcagccacg tggtgtgggc cttgcaaaat gatcaagcct     120
ttctttcatt ccctctctga aaagtattcc aacgtgatat tccttgaagt agatgtggat     180
gactgtcagg atgttgcttc agagtgtgaa gtcaaatgca tgccaacatt ccagttttt      240 aagaagggac aaaaggtggg tgaattttct ggagccaata ggaaaagct tgaagccacc     300 attaatgaat tagtctaa                                                   318

<210> SEQ ID NO 3
<211> LENGTH: 115
<212> TYPE: PRT
<213> ORGANISM: Homo sapiens

<400> SEQUENCE: 3

Met Pro Met Phe Ile Val Asn Thr Asn Val Pro Arg Ala Ser Val Pro
1               5                   10                  15

Asp Gly Phe Leu Ser Glu Leu Thr Gln Gln Leu Ala Gln Ala Thr Gly
            20                  25                  30

Lys Pro Pro Gln Tyr Ile Ala Val His Val Val Pro Asp Gln Leu Met
        35                  40                  45

Ala Phe Gly Gly Ser Ser Glu Pro Cys Ala Leu Cys Ser Leu His Ser
    50                  55                  60

Ile Gly Lys Ile Gly Gly Ala Gln Asn Arg Ser Tyr Ser Lys Leu Leu
65                  70                  75                  80

Cys Gly Leu Leu Ala Glu Arg Leu Arg Ile Ser Pro Asp Arg Val Tyr
                85                  90                  95

Ile Asn Tyr Tyr Asp Met Asn Ala Ala Asn Val Gly Trp Asn Asn Ser

-continued

```
        100                 105                 110

Thr Phe Ala
        115

<210> SEQ ID NO 4
<211> LENGTH: 4
<212> TYPE: PRT
<213> ORGANISM: Unknown
<220> FEATURE:
<223> OTHER INFORMATION: OTHER INFORMATION: active site of polypeptides
      belonging to a thioredoxin family

<400> SEQUENCE: 4

Cys Gly Pro Cys
1

<210> SEQ ID NO 5
<211> LENGTH: 4
<212> TYPE: PRT
<213> ORGANISM: Unknown
<220> FEATURE:
<223> OTHER INFORMATION: OTHER INFORMATION: active site of polypeptides
      belonging to a thioredoxin family

<400> SEQUENCE: 5

Cys Pro Tyr Cys
1

<210> SEQ ID NO 6
<211> LENGTH: 4
<212> TYPE: PRT
<213> ORGANISM: Unknown
<220> FEATURE:
<223> OTHER INFORMATION: OTHER INFORMATION: active site of polypeptides
      belonging to a thioredoxin family

<400> SEQUENCE: 6

Cys Pro His Cys
1

<210> SEQ ID NO 7
<211> LENGTH: 4
<212> TYPE: PRT
<213> ORGANISM: Unknown
<220> FEATURE:
<223> OTHER INFORMATION: OTHER INFORMATION: active site of polypeptides
      belonging to a thioredoxin family

<400> SEQUENCE: 7

Cys Pro Pro Cys
1
```